United States Patent
Sela et al.

(10) Patent No.: US 10,102,681 B2
(45) Date of Patent: Oct. 16, 2018

(54) METHOD, SYSTEM AND APPARATUS FOR ADJUSTING IMAGE DATA TO COMPENSATE FOR MODALITY-INDUCED DISTORTION

(71) Applicants: Gal Sela, Toronto (CA); Sean Jy-shyang Chen, Toronto (CA); Simon Kenley Alexander, Toronto (CA); Alexander Gyles Panther, Toronto (CA)

(72) Inventors: Gal Sela, Toronto (CA); Sean Jy-shyang Chen, Toronto (CA); Simon Kenley Alexander, Toronto (CA); Alexander Gyles Panther, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 263 days.

(21) Appl. No.: 15/107,015

(22) PCT Filed: Jul. 29, 2015

(86) PCT No.: PCT/IB2015/055728
§ 371 (c)(1),
(2) Date: Jun. 21, 2016

(87) PCT Pub. No.: WO2017/017498
PCT Pub. Date: Feb. 2, 2017

(65) Prior Publication Data
US 2018/0197346 A1 Jul. 12, 2018

(51) Int. Cl.
*G06K 9/00* (2006.01)
*G06T 19/20* (2011.01)
(Continued)

(52) U.S. Cl.
CPC .............. *G06T 19/20* (2013.01); *G06T 7/344* (2017.01); *G06T 15/08* (2013.01); *A61B 5/055* (2013.01);
(Continued)

(58) Field of Classification Search
CPC ......... G06T 19/20; G06T 7/344; G06T 15/08; G06T 2207/10081; G06T 2207/30016; A61B 5/055; A61B 6/032
See application file for complete search history.

(56) References Cited

U.S. PATENT DOCUMENTS 6,275,038 B1 *  8/2001  Harvey ............ G01R 33/56563
                                                324/307
6,288,540 B1 *  9/2001  Chen ................ G01R 33/56341
                                                324/300
(Continued)

FOREIGN PATENT DOCUMENTS

WO      2014031531 A1    2/2014

OTHER PUBLICATIONS

International Search Report dated Jan. 8, 2016 issued from the Canadian Intellectual Property Office relating to corresponding PCT International Application No. PCT/IB2015/055728.
(Continued)

*Primary Examiner* — Samir Ahmed
(74) *Attorney, Agent, or Firm* — Perry + Currier

(57) ABSTRACT

A method of generating adjusted image data to compensate for modality-induced distortion includes, at a processor: receiving a three-dimensional image captured with a first imaging modality and including (i) distorted surface image data depicting a surface of an object and (ii) distorted volume image data depicting a volume of the object; extracting the distorted surface image data from the three-dimensional image; receiving reference surface image data cap-
(Continued)

tured with a second imaging modality and depicting the surface of the object; determining a surface transformation for registering the distorted surface image data with the reference surface image data; determining a volume transformation informed by the surface transformation; generating an adjusted three-dimensional image by applying the volume transformation to the three-dimensional image; and storing the adjusted three-dimensional image in the memory.

18 Claims, 7 Drawing Sheets

(51) Int. Cl.
    *G06T 15/08*     (2011.01)
    *G06T 7/33*     (2017.01)
    *A61B 6/03*     (2006.01)
    *A61B 5/055*     (2006.01)

(52) U.S. Cl.
    CPC ..... *A61B 6/032* (2013.01); *G06T 2207/10081* (2013.01); *G06T 2207/10088* (2013.01); *G06T 2207/30016* (2013.01)

(56) References Cited

U.S. PATENT DOCUMENTS

| | | | |
|---|---|---|---|
| 6,320,380 B1* | 11/2001 | Wu | G01R 33/5615 324/307 |
| 6,445,182 B1* | 9/2002 | Dean | G01R 33/4822 324/307 |
| 6,542,858 B1* | 4/2003 | Grass | C40B 30/02 703/2 |
| 6,594,516 B1 | 7/2003 | Steckner et al. | |
| 7,782,998 B2* | 8/2010 | Langan | G01N 23/046 378/8 |
| 2005/0096515 A1 | 5/2005 | Geng | |
| 2009/0161931 A1* | 6/2009 | Tao | G06T 7/33 382/131 |
| 2009/0190809 A1* | 7/2009 | Han | G06K 9/48 382/128 |
| 2011/0187367 A1* | 8/2011 | Feiweier | G01R 33/44 324/309 |
| 2012/0155734 A1 | 6/2012 | Barratt et al. | |
| 2013/0259335 A1 | 10/2013 | Mallya et al. | |
| 2013/0285653 A1* | 10/2013 | Zhou | G01R 33/56572 324/307 |
| 2014/0369584 A1* | 12/2014 | Fan | A61B 6/501 382/131 |

OTHER PUBLICATIONS

Written Opinion dated Jan. 8, 2016 issued from the Canadian Intellectual Property Office relating to corresponding PCT International Application No. PCT/IB2015/055728.

* cited by examiner

METHOD, SYSTEM AND APPARATUS FOR ADJUSTING IMAGE DATA TO COMPENSATE FOR MODALITY-INDUCED DISTORTION

FIELD

The specification relates generally to the field of medical imaging, and specifically to a method, system and apparatus for adjusting image data to compensate for modality-induced distortion.

BACKGROUND

Imaging modalities such as magnetic resonance imaging (MRI) can introduce spatial distortions in the representation as a consequence of the imaging physics. Such distortions can reduce the spatial fidelity of the images (for example, preoperative images of a patient undergoing a medical procedure) and consequently the accuracy of registration to other images, medical navigation and tracking systems, and the like. Conventional attempts to reduce the effects of the above-mentioned distortions include physically based correction based on additional information (such as MRI field mapping) and/or image based techniques, typically by registering to an image of the same volume, captured using a different imaging modality with better spatial accuracy such as computed tomography (CT). Such conventional approaches may require significantly more scanning time, imaging on multiple pieces of equipment and, in the case of modalities like CT, may entail additional radiation exposure for the patient.

SUMMARY

According to an aspect of the specification, a method is provided of generating adjusted image data to compensate for modality-induced distortion in a computing device having a processor interconnected with a memory and a display. The method includes, a the processor: receiving a three-dimensional image captured with a first imaging modality and including (i) distorted surface image data depicting a surface of an object and (ii) distorted volume image data depicting a volume of the object; extracting the distorted surface image data from the three-dimensional image; receiving reference surface image data captured with a second imaging modality and depicting the surface of the object; determining a surface transformation for registering the distorted surface image data with the reference surface image data; determining a volume transformation informed by the surface transformation; generating an adjusted three-dimensional image by applying the volume transformation to the three-dimensional image; and storing the adjusted three-dimensional image in the memory.

According to another aspect of the specification, a computing device is provided. The computing device includes: a memory; a display; and a processor interconnected with the memory and the display, the processor configured to: receive a three-dimensional image captured with a first imaging modality and including (i) distorted surface image data depicting a surface of an object and (ii) distorted volume image data depicting a volume of the object; extract the distorted surface image data from the three-dimensional image; receive reference surface image data captured with a second imaging modality and depicting the surface of the object; determine a surface transformation for registering the distorted surface image data with the reference surface image data; determine a volume transformation informed by the surface transformation; generate an adjusted three-dimensional image by applying the volume transformation to the three-dimensional image; and store the adjusted three-dimensional image in the memory.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
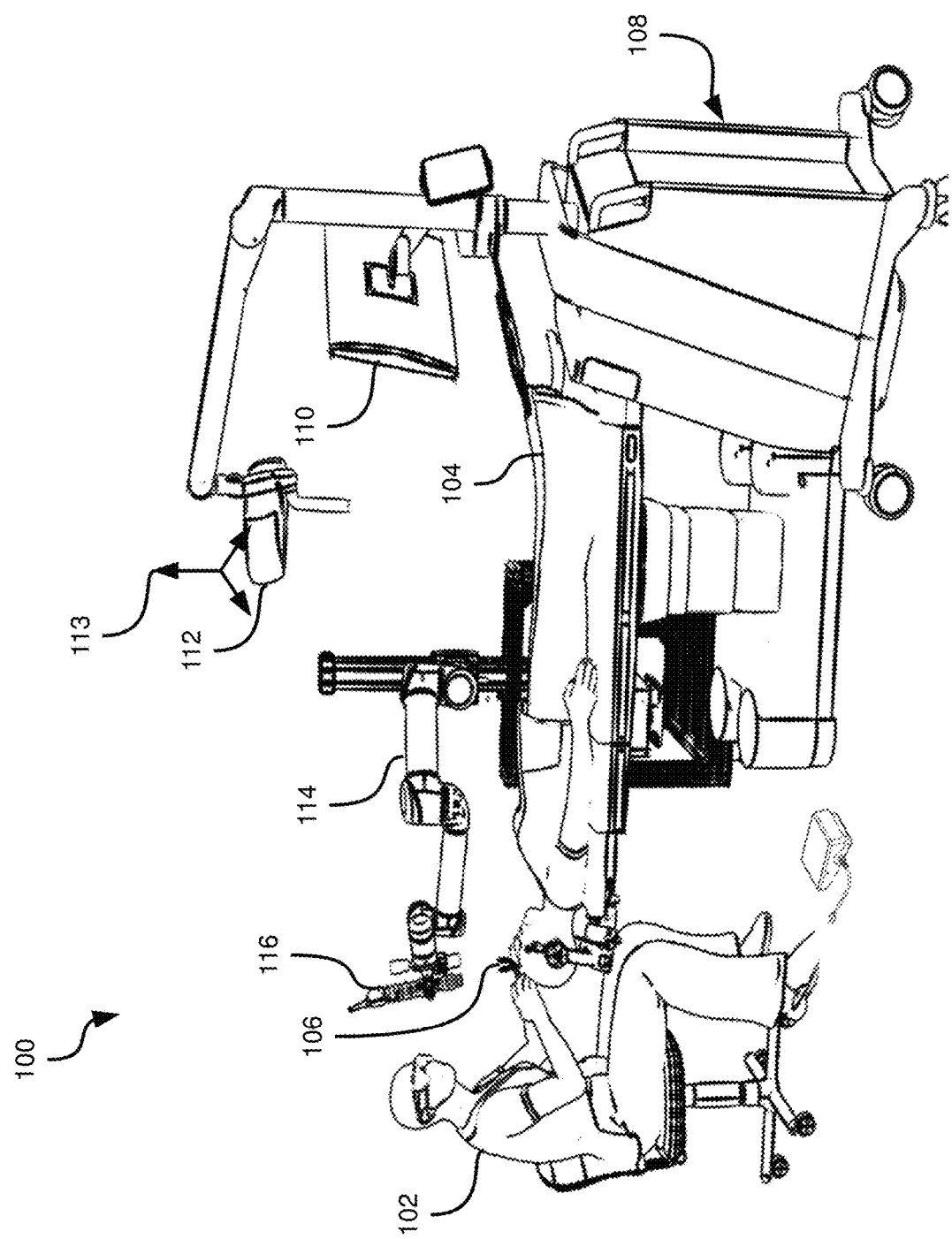
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues, including other portions of the cerebrospinal system as well as any other suitable tissue. Thus, when the brain of patient 104 is mentioned below, it is simply an example of the various tissues in connection with which the systems and methods herein may be implemented. Further, the systems and methods described herein need not be restricted to use in minimally invasive surgery, but can also be employed in conjunction with other surgical techniques.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like. Additional instruments may be employed to conduct the procedure that do not extend into access port 106, such as laser ablation devices (which can emit laser light into access port 106).

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 102, any of the above-mentioned surgical tools and instruments, or any combination thereof. Such markers, also referred to as fiducial markers, may also be mounted on patient 104, for example at various points on the head of patient 104. Tracking system 112 may therefore include a camera (e.g. a stereo camera) and a computing device (either the same computing device as mentioned above or a separate computing device) configured to locate the fiducial markers in the images captured by the camera, and determine the spatial positions of those markers within the operating theatre. The spatial positions may be provided by tracking system 112 to the computing device in equipment tower 108 for subsequent use. The positions determined by tracking system 112 may be provided in a frame of reference 113 (that is, a coordinate system) centered at a point of origin within the operating room.

The nature of the markers and the camera are not particularly limited. For example, the camera may be sensitive to infrared (IR) or near-infrared (NIR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or unpulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 102 by robotic arm 114, and may capture images of the brain of patient 104 for presentation on display 110. The movement of robotic arm 114 to place external scope 116 correctly over access port 102 may be guided by tracking system 112 and the computing device in equipment tower 108. In other words, one or both of robotic arm 114 and scope 116 bear markers that are detectable by tracking system 112. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of the brain or other tissues of patient 104. Such preoperative images may be collected using any of a variety of imaging modalities, including Magnetic Resonance Imaging (MRI). During the procedure, additional images (referred to as intraoperative images) may be collected of the brain or other tissues of patient 104, using any of the above-mentioned additional imaging devices.

In some procedures, intraoperatively-collected images may be presented on display 110. Such intraoperative images can be presented on display 110 overlaid on a preoperative image, such as an MRI image, in order to facilitate the tracking of instruments and the execution of a surgical plan (which may, for example, be marked on the preoperative image).

However, some imaging modalities—notably, MRI—can introduce spatial distortions into images collected via those modalities. Such distortions in preoperative MRI images can reduce the spatial fidelity of the MRI images, and as a result can also reduce the accuracy of registration to other images, navigation and tracking systems (e.g. system 112), and the like. Such distortions can also reduce the accuracy with which the positions of instruments tracked by tracking system 112 are shown on display 110 in relation to the preoperative image. Therefore, the computing device mentioned above is configured to generate adjusted image data from MRI images, the adjusted image data having greater spatial fidelity than the original MRI images, to compensate for the distortions contained in the original images. The computing device can be configured to generate such adjusted image data without requiring the collection of image data depicting the full volume depicted in the MRI images.

Figure 2:
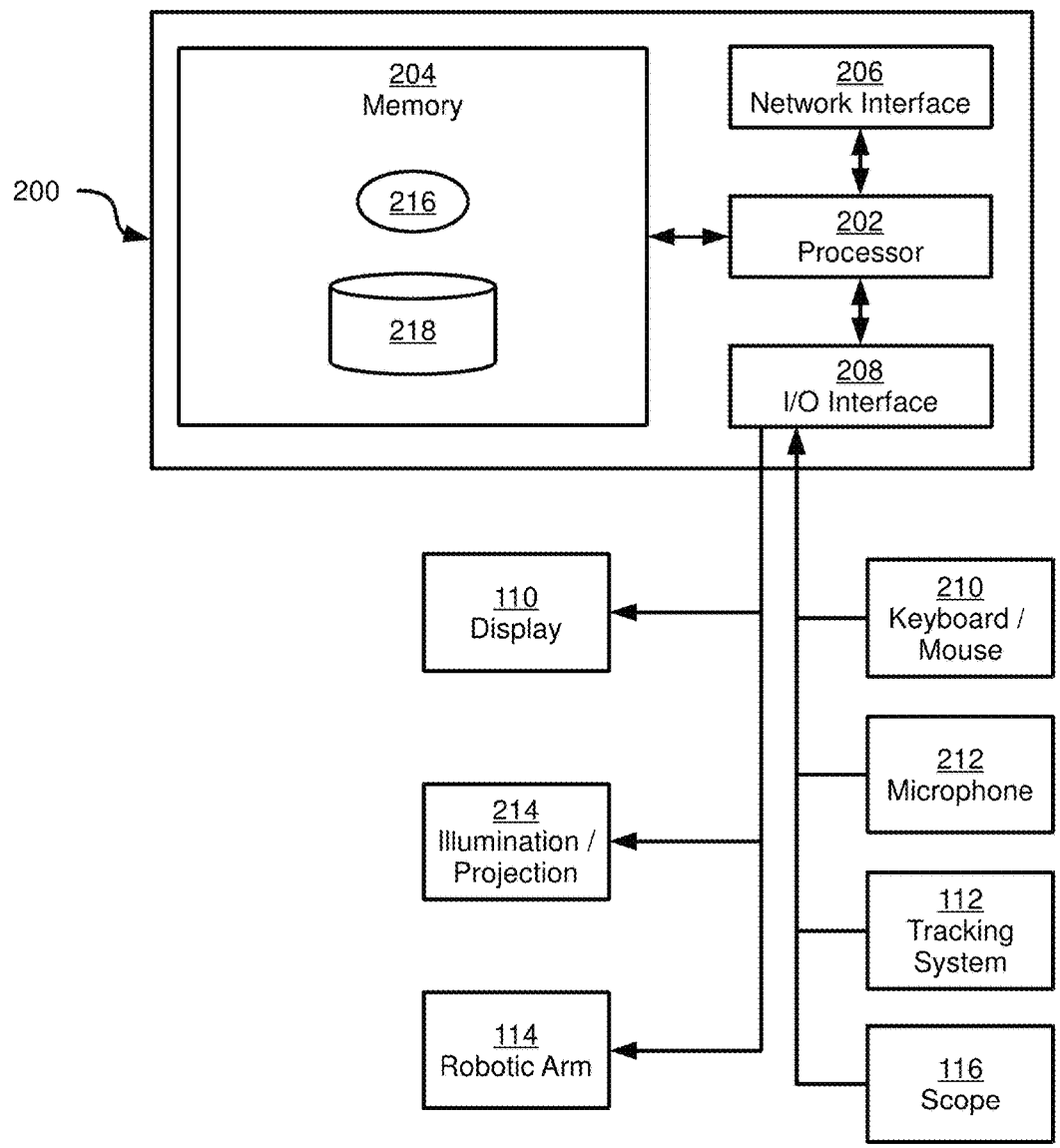
FIG. 2 depicts a computing device of the operating theatre of FIG. 1, according to a non-limiting embodiment.

Before a discussion of the above-mentioned functionality of the computing device, a description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Similarly, computing device 200 can be connected to the additional imaging devices mentioned above via interface 208. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, an image processing application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as images captured using modalities such as MRI, and the like.

As mentioned above, computing device 200 is configured, via the execution of application 216 by processor 202, to generate adjusted image data from distorted images (such as MRI images) to compensate for the distortions contained in those images. Those functions will be described in further detail below.

Figure 3:
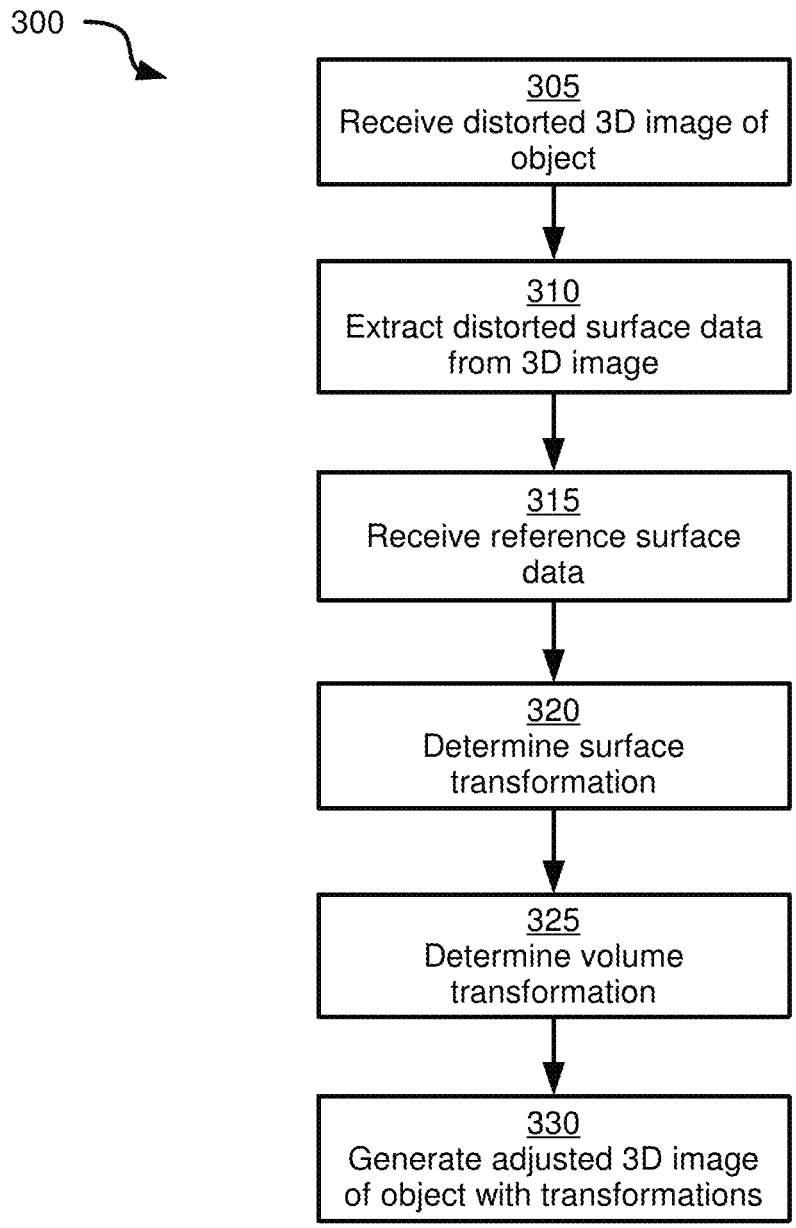
FIG. 3 depicts a method of generating adjusted image data, according to a non-limiting embodiment.

Referring now to FIG. 3, a method 300 of generating adjusted image data is depicted. The performance of method 300 will be described in connection with its performance on computing device 200, although it is contemplated that method 300 can also be performed on other suitable computing devices.

Beginning at block 305, computing device 200 is configured to receive a three-dimensional image captured using a first imaging modality. In the present example, the first imaging modality is MRI, but in other embodiments, any suitable imaging modality may be employed. Other suitable imaging modalities may include ultrasound tomography (UT) imaging, X-ray imaging, positron emission tomography (PET) imaging, and computerized axial tomography (CAT/CT) imaging. The three-dimensional image can be received via a variety of mechanisms. For example, at block 305 processor 202 can be configured to retrieve the three-dimensional image from memory 204 (e.g. from patient data repository 218). In other embodiments, computing device 200 can be connected to an imaging apparatus such as an MRI scanner, and the performance of block 305 can include receiving the image directly from the MRI scanner (indeed, in some embodiments, computing device 200 can operate to control the MRI scanner to capture the image). In still other embodiments, computing device 200 can receive the three-dimensional image from another computing device (not shown) via network interface 206.

The three-dimensional image includes distorted surface image data depicting a surface of an object, and distorted volume image data depicting a volume of the object. In the present example, the object in question is the head of patient 104, or at least a portion thereof.

Figure 4:
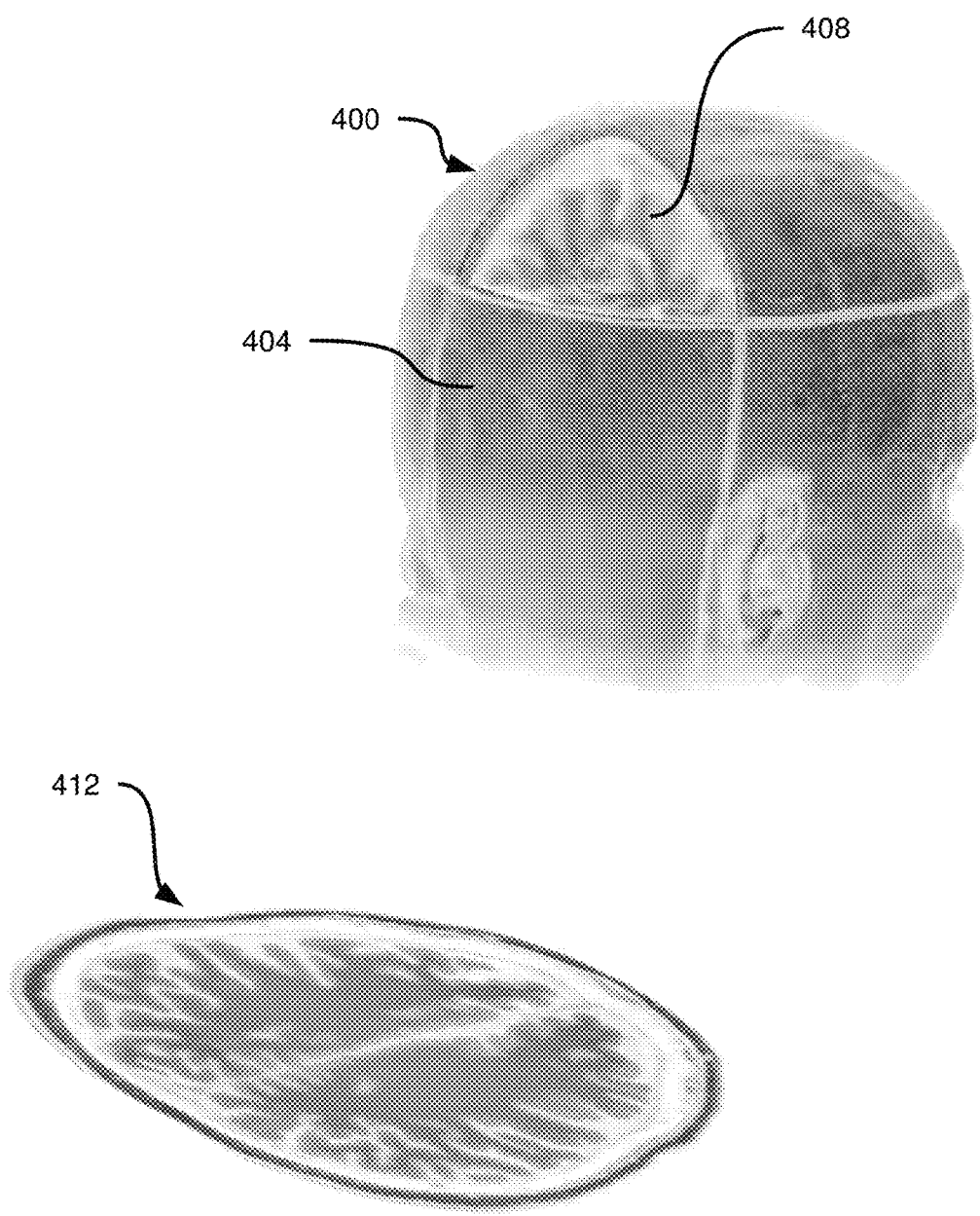
FIG. 4 depicts example distorted surface and volume image data depicting an object, according to a non-limiting embodiment.

Turning to FIG. 4, an example three-dimensional image 400 is shown, as received at block 305. As seen in FIG. 4, image 400 includes surface data 404 depicting a surface of the head of patient 104 (e.g. the outer surface of the skull of patient 104), and volume data 408 depicting a volume (i.e. the interior of the head of patient 104, including the brain of patient 104). As will be apparent to those skilled in the art, image 400 can include a plurality of layers (an example layer 412 is shown) each containing a portion of surface data 404 and volume data 408. Image 400 consists of the plurality of layers stacked together.

As noted earlier, the data in image 400 may be distorted. That is, surface data 404 and volume data 408 may not accurately depict the corresponding tissues of patient 104, but may instead provide distorted depictions of patient 104.

Returning to FIG. 3, at block 310 computing device 200 is configured to extract the distorted surface data 404 from the three-dimensional image received at block 305. For example, processor 202 can be configured to extract the distorted surface data 404 by selecting, from image 400, the outer-most points or voxels. The selected data can be added to an extracted surface image, while the remaining data (that is, the volume data 408) is ignored.

At block 315, computing device 200 is configured to receive reference surface image data in the form of a reference image captured using a different imaging modality than that employed to capture image 400, and depicting the surface of the same object as depicted by image 400. In general, the reference surface data has two characteristics: (1) it is captured using an imaging modality that is less prone (or entirely immune to) distortions than the modality used to capture image 400, and thus more accurately represents the surface of the depicted object (i.e. the head of patient 104); and (2) it does not include volume image data. That is, the reference image depicts only the surface of the object in question.

Figure 5:
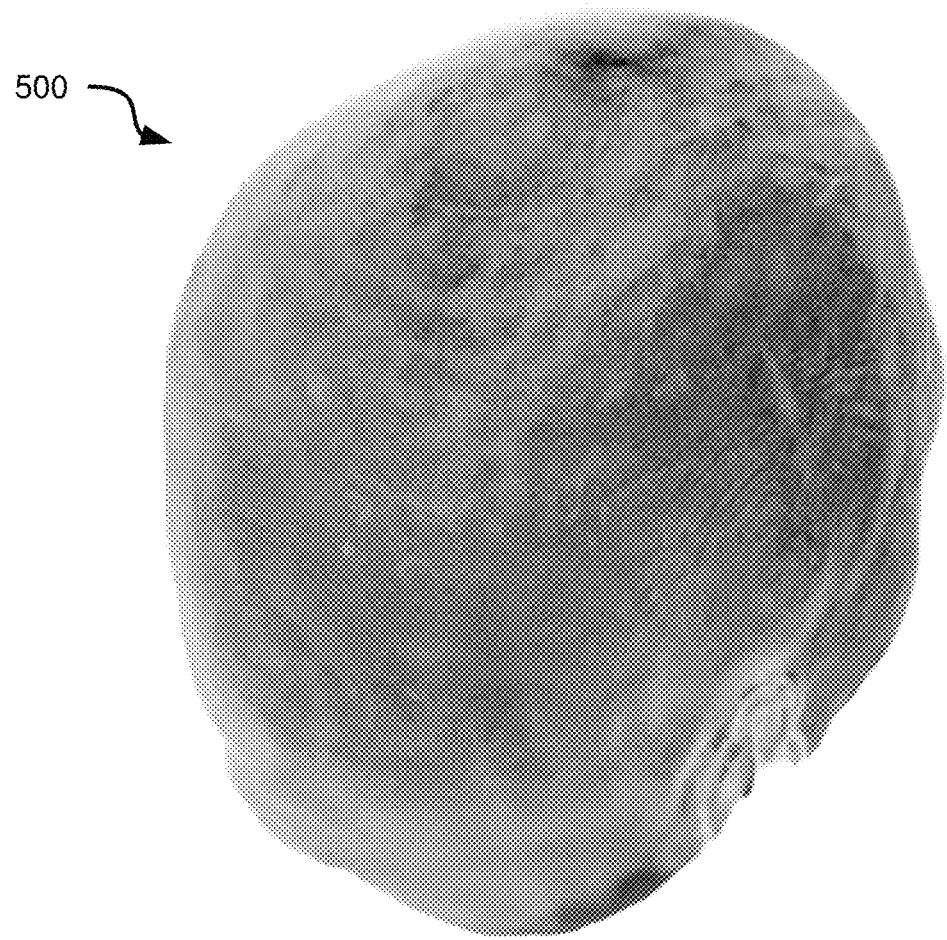
FIG. 5 depicts example reference surface image data, according to a non-limiting embodiment.

Various imaging modalities are contemplated for the reference image. For example, the reference image can be captured using a three-dimensional surface scanner, a laser line scanner, a laser range finder, touch-based range-finding devices, ultrasonic scanning devices, or any suitable combination thereof. In some embodiments, the reference image can include a point cloud containing a plurality of discrete depth measurements (e.g. taken with a laser range finder). An example of a reference image 500 is shown in FIG. 5. As with image 400, the receipt of the reference surface image data can occur by a variety of processes. In some embodiments, the reference surface data is received at computing device 200 from an imaging device (e.g. a laser-based three-dimensional scanner) before or at the start of the surgical procedure that patient 104 is to undergo. In other embodiments, however, the reference surface image data can be received from another computing device, for instance via network interface 206.

At block 320, computing device 200 is configured to determine a surface transformation for registering distorted surface data 404 with reference surface data 500. Registering distorted surface data 404 with reference surface data 500 involves altering distorted surface data 404 by any of a variety of mechanisms (e.g. rotation, translation, scaling, and the like) to align distorted surface data 404 with reference surface data 500. In other words, the transformation determined at block 320, when applied to distorted surface data 404, repositions the pixels or voxels of distorted surface data 404 to be co-located with pixels or voxels of reference surface data 500 that depict the same portions of the object (i.e. the head of patient 104).

Any suitable image registration technique can be applied by processor 202 at block 320 to determine the surface transformation. For example, processor 202 can be configured to place distorted surface data 404 in a common coordinate system with reference surface data 500, and to identify a plurality of point pairs (each pair including a point in distorted surface image data 404 and a point in reference surface image data 500). Each point pair depicts substantially the same portion of the object (e.g. both points in a pair depict the same portion of the surface of patient 104's head). The identification of point pairs can be performed according to any suitable process, including feature-based and intensity-based registration techniques.

For each point pair, processor 202 can then be configured to determine a distance between the two points in the common coordinate system. The combined distance between all identified point pairs (or, for example, the combination of the square of the distances between all identified point pairs) can be employed by processor 202 as a metric to determine how accurate the registration of distorted surface data 404 to reference surface data 500 is.

Having established the above-mentioned distances, processor 202 can be configured to select any suitable transformation function, or combination of transformation functions. As noted above, global, rigid transformation functions such as translations, rotations and scaling can be employed. In other embodiments, a wide variety of other transformation functions can also be employed, including functions that operate on subsets of the points in distorted surface data 404 (rather than acting globally), such as local deformation vectors, and including non-rigid affine functions.

Processor 202 can be configured to optimize the parameters of the selected transformation functions by altering the parameters, applying the transformation to distorted surface data 404, repeating the computation of the above-mentioned distances, and repeating the alteration of parameters, and application of the transformation to minimize the distances.

Having determined a surface transformation at block 320, processor 202 is then configured to determine a volume transformation at block 325. While the surface transformation determined by processor 202 at block 320 is selected to reduce or eliminate the distortions introduced into surface data 404 by the imaging modality used to capture image 400 (MRI, in the present example) the volume transformation determined at block 325 is selected to reduce or eliminate the distortions introduced into volume data 408 by that same imaging modality. However, as will now be apparent to those skilled in the art, while reference surface data 500 was available in the determination of the surface transformation, no reference volume data is available.

Therefore, at block 325, processor 202 is configured to determine the volume transformation based on—that is, informed by—the surface transformation from block 320. A variety of mechanisms are contemplated for determining a volume transformation based on the surface transformation determined at block 320. In some embodiments, processor 202 is configured to use the surface transformation as the volume transformation. For example, if the surface transformation determined at block 320 was a rotation of distorted surface data 404 about a given axis, then at block 325 processor 202 can be configured to set the volume transformation as the same rotation about the same axis.

In other embodiments, processor 202 can be configured to set the volume transformation as a localized version of the surface transformation. For example, when the surface transformation is a global scaling of 90% (that is, a reduction in size of the original distorted surface data), the volume transformation can be set as a scaling of 70% (that is, a greater reduction in size for distorted volume data 408). The volume transformation, in such embodiments, need not be applied to the entirety of distorted volume data 408. For example, processor 202 can be configured to apply the above-mentioned 70% scaling to only a portion of distorted volume data 408, such as the portion of distorted volume data 408 within a certain distance of distorted surface data 404. In other words, the outer portion of distorted volume data 408 may be "squeezed" to fit within the scaled-down distorted surface data, and the remainder of distorted volume data 408 may be left unchanged. Note that such transformations need not be global in effect or application. A variety of other volume transformations can also be generated from the surface transformation, including any suitable non-linear transformation (in contrast to the linear scaling mentioned above), such as transformations based on deformation fields, point-based thin-plate splines and the like.

In some embodiments, the accuracy of the volume transformation may be improved (that is, the distortions in distorted volume data 408 may be better corrected) by employing more complex determinations at block 325. Two examples of such determinations will be discussed below in greater detail.

Figure 6:
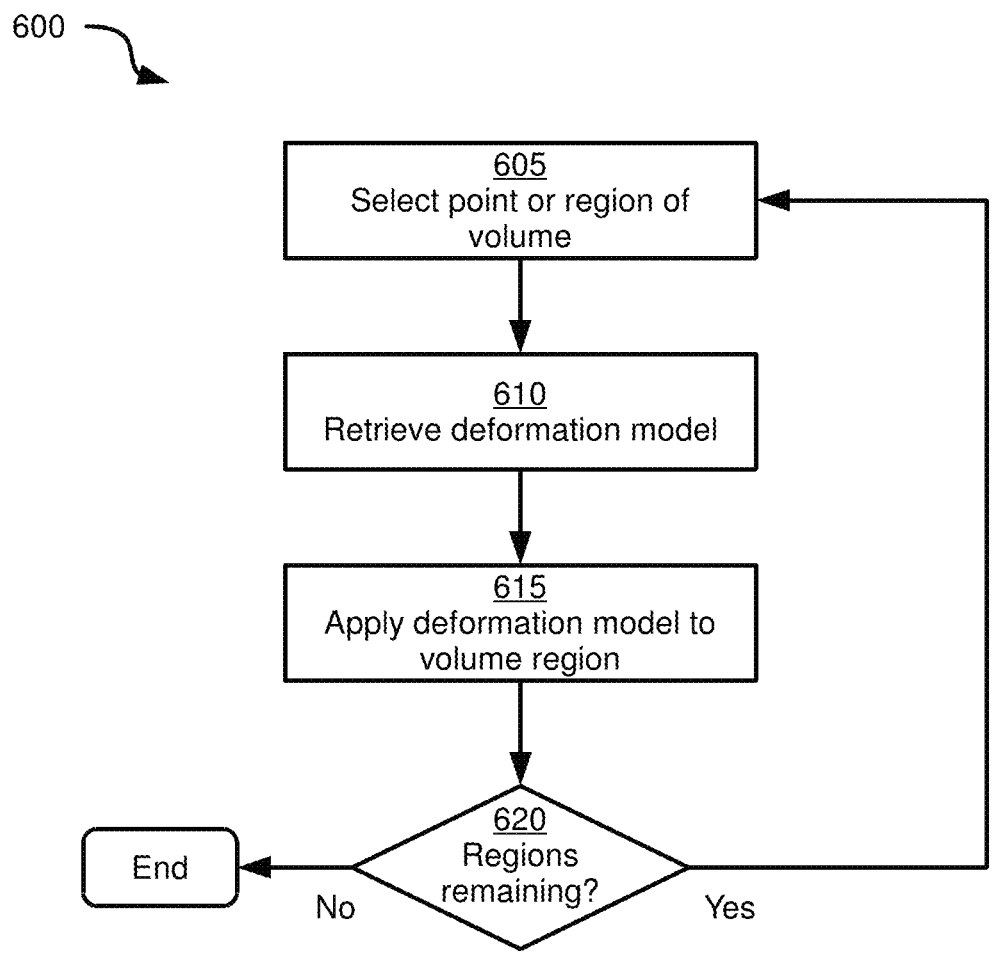
FIG. 6 depicts a method of performing block 325 of the method of FIG. 3, according to a non-limiting embodiment.

Referring to FIG. 6, a method 600 of performing block 325 is illustrated. At block 605, processor 202 is configured to select a point (e.g. a voxel) or a region (that is, a set of points or voxels) within distorted volume data 408. At block 610, processor 202 is configured to retrieve a deformation model for the selected region of distorted volume data. The deformation model can be stored in memory 204, and can include identifications of surface regions whose deformations are correlated with the selected volume region. The deformation model can include such identifications for each region of the volume. The deformation model can also include indications of how strongly each identified surface region correlates with deformation of the volume region. In other words, the deformation model is a probabilistic model of how various surface deformations are likely to affect the volume.

The deformation model can be constructed previously, for example by examining a plurality of distorted images and corresponding non-distorted images of the same objects (e.g. a plurality of MRI images and corresponding CT images). The actual deformations between the surfaces and volumes of each image pair can thus be determined, and correlations between surface region deformations and volume region deformations can be identified. Thus, at block 610 processor 202 need only retrieve the previously computed correlations between the selected volume region and one or more surface regions.

At block 615, processor 202 can be configured to apply the deformation model to the selected volume region, for example by applying the same deformations as determined at block 320 for the surface regions corresponding to the selected volume region in the deformation model. When regions of distorted volume data 408 remain to be processed at block 620, processor returns to block 605 to select another volume region. Otherwise, the performance of method 600 ends, and processor 202 returns to method 300.

More generally, computing device 200 can store, in memory, any suitable correspondence between surface deformations and volume deformations. Computing device 200 can store, in memory 204, a plurality of volume transformations corresponding to different ones of a plurality of surface transformations; and can determine the volume transformation at block 325 by retrieving, from memory 204, the volume transformation corresponding to the surface transformation determined at block 320.

Figure 7:
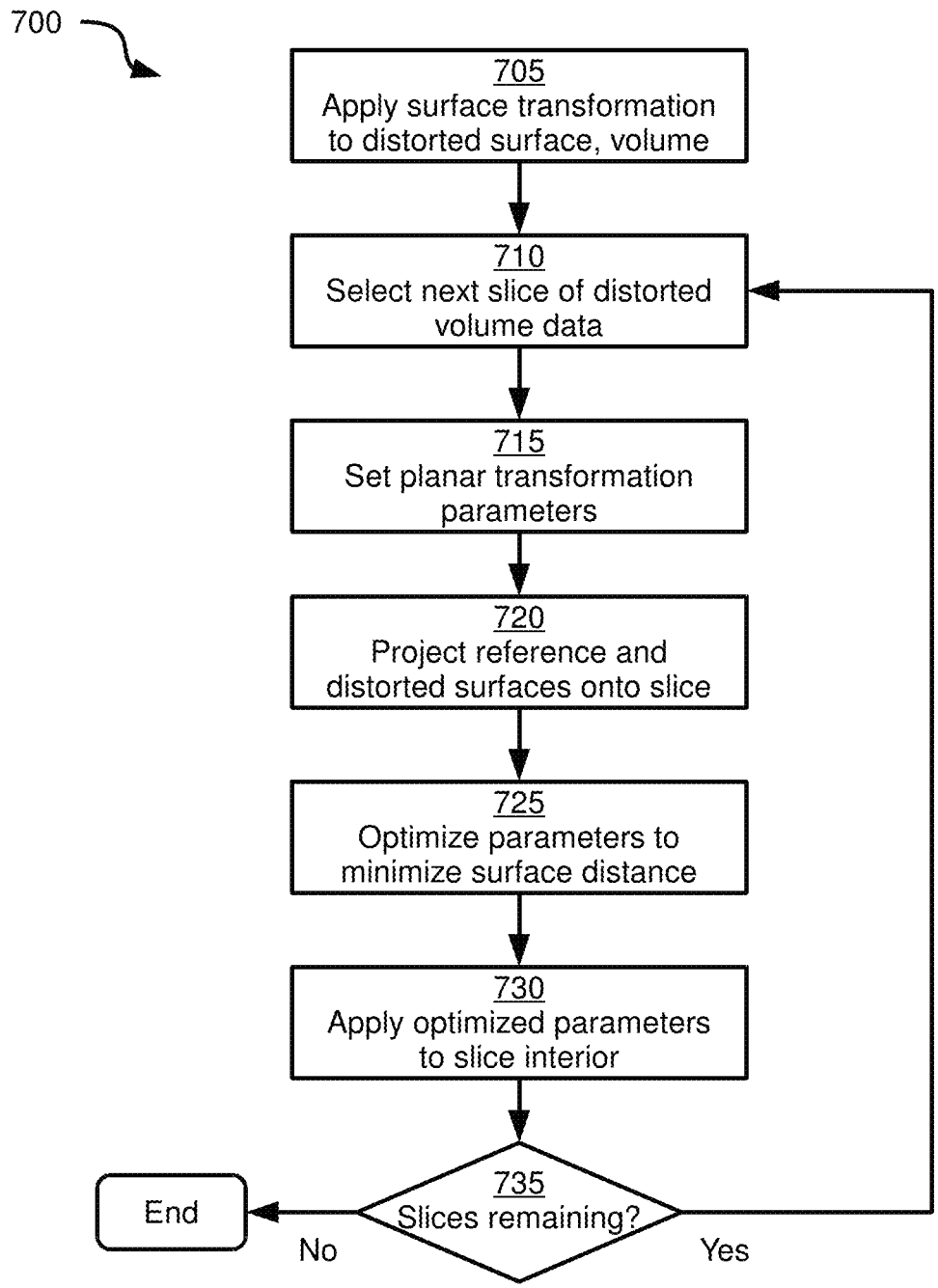
FIG. 7 depicts a method of performing block 325 of the method of FIG. 3, according to another non-limiting embodiment.

Referring now to FIG. 7, a further method 700 of performing block 325 is depicted. Method 700 can be applied to three-dimensional images acquired as a collection of slices, such as MRI image 400, shown in FIG. 4. The determination of a volume transformation through the performance of method 700 includes determining a plurality of volume transformations (one for each slice of the original image 400), and can constrain the transformations based on known characteristics of the imaging modality used to capture image 400.

At block 705, processor 202 is configured to apply the surface transformation determined at block 320 to distorted surface data 404 and distorted volume data 408 (that is, to the entirety of image 400). At block 710, processor 202 is configured to select a slice of the distorted volume data (as transformed via the performance of block 705).

Having selected a slice of distorted volume data 408, at block 715 processor 202 is configured to set slice-specific transformation parameters. The nature of the transformation parameters is not particularly limited. In the present example, the transformation parameters are based on known characteristics of the imaging modality used to capture image 400 (e.g. MRI). Thus, in the present example, the transformation parameters include a translation parameter, a scaling parameter, and a shear parameter. This selection of parameters reflects certain known distortions introduced by MRI scanning, such as those discussed in Haselgrove and Moore, "Correction for distortion of echo-planar images used to calculate the apparent diffusion coefficient", *Magn Reson Med.* 1996 December; 36(6):960-4, the contents of which are hereby incorporated by reference.

The performance of block 715 includes selecting a transformation function. In the present example, the function can be: $Y'=(S*Y+T0+T1*X)/S$, where Y is the phase-encode direction coordinate (which can be retrieved from the metadata, such as DICOM data, of image 400). Y' is the transformed phase-encode direction coordinate of a point; S is the above-mentioned scaling parameter; T0 is the above-mentioned scaling parameter, and T1 is the above-mentioned shear parameter. X is the readout direction coordinate. Final scaling by 1/S is done to conserve energy. This amounts to a slice specific affine transformation of the data.

At block 720, processor 202 is configured to project reference surface data 500 and distorted surface data 404 as modified by block 705 onto the plane of the current slice selected at block 710. Although the projected portion of distorted surface data has already been transformed in an attempt to register with reference surface data 500 through the performance of blocks 320 and 705, in at least some slices the transformed distorted surface data will still not align perfectly with the reference surface data.

Therefore, at block 725 processor 202 is configured to optimize the parameters set at block 715 to minimize the distance between the transformed distorted surface data and the reference surface data for the selected slice. In effect, the performance of block 725 is a slice-specific performance of the optimization discussed earlier in connection with block 320, the exception that the parameters available for optimization are selected to reflect characteristics of the imaging modality.

When the distance between the transformed distorted surface data and the reference surface data has been minimized, at block 730 processor 202 is configured to apply the optimized transformation parameters to the remainder of the slice (that is, to the distorted volume data in the selected slice). The above process is then repeated until no further slices remain to be processed (that is, until the determination at block 735 is negative).

Returning to FIG. 3, at block 330 processor 202 is configured to generate an adjusted three dimensional image of the object depicted in image 400, by applying the volume transformation from block 325 to the three-dimensional image (that is, to the distorted surface data and the distorted volume data). The adjusted three dimensional image can be stored in memory 204 (e.g. in repository 218). Processor 202 can also be configured to present the adjusted three-dimensional image on display 110.

Various advantages to the above embodiments will now be apparent to those skilled in the art. For example, the adjustment of distorted image data via the techniques described above, in contrast to the use of a full three-dimensional reference image including volume data (such as a CT image), may be achievable with reduced data storage requirements. The above systems and methods may also reduce the need for patient exposure to radiation, and the use of costly equipment to perform time-consuming imaging procedures to collect the reference image data.

The scope of the claims should not be limited by the embodiments set forth in the above examples, but should be given the broadest interpretation consistent with the description as a whole.

We claim:

1. A method of generating adjusted image data to compensate for modality-induced distortion in a computing device having a processor interconnected with a memory and a display, comprising, at the processor:
receiving a three-dimensional image captured with a first imaging modality and including (i) distorted surface image data depicting a surface of an object and (ii) distorted volume image data depicting a volume of the object;
extracting the distorted surface image data from the three-dimensional image;
receiving reference surface image data captured with a second imaging modality and depicting the surface of the object;
determining a surface transformation for registering the distorted surface image data with the reference surface image data;
determining a volume transformation informed by the surface transformation, by:
applying the surface transformation to the distorted volume image data;
for each of a plurality of slices in the distorted volume image data;
retrieving control parameters of the first imaging modality from the three-dimensional image;
selecting a planar transformation based on the control parameters;
projecting the reference surface image data onto a plane corresponding to the slice; and
optimizing the planar transformation to minimize an error level between the slice and the projected reference surface image data;
generating an adjusted three-dimensional image by applying the volume transformation to the three-dimensional image; and
storing the adjusted three-dimensional image in the memory.

2. The method of claim 1, wherein the first imaging modality is magnetic resonance imaging (MRI).

3. The method of claim 1, wherein the second imaging modality is three-dimensional surface scanning.

4. The method of claim 1, wherein determining the surface transformation comprises:
identifying a plurality of point pairs, each pair including a point in the distorted surface image data and a point in the reference surface image data, each point pair depicting the same portion of the surface of the object; and, for each point pair:
determining a distance between the point in the distorted surface image data and the point in the reference surface image data.

5. The method of claim 4, wherein determining the surface transformation further comprises:
selecting a transformation function; and
optimizing the transformation function to minimize the distance.

6. The method of claim 1, further comprising:
storing, in the memory, a plurality of volume transformations corresponding to different ones of a plurality of surface transformations;
determining the volume transformation by retrieving, from the memory, the volume transformation corresponding to the determined surface transformation.

7. The method of claim 1, wherein the volume transformation applies the same transformation function as applied by the surface transformation.

8. The method of claim 1, wherein the volume transformation is a localized version of the surface transformation, and wherein applying the volume transformation comprises applying the volume transformation to only a subset of the distorted volume image data.

9. The method of claim 1, further comprising:
at the processor, controlling the display to present the adjusted three-dimensional image.

10. A computing device, comprising:
a memory;
a display; and
a processor interconnected with the memory and the display, the processor configured to:
receive a three-dimensional image captured with a first imaging modality and including (i) distorted surface image data depicting a surface of an object and (ii) distorted volume image data depicting a volume of the object;
extract the distorted surface image data from the three-dimensional image;
receive reference surface image data captured with a second imaging modality and depicting the surface of the object;
determine a surface transformation for registering the distorted surface image data with the reference surface image data;
determine a volume transformation informed by the surface transformation, by:
applying the surface transformation to the distorted volume image data;
for each of a plurality of slices in the distorted volume image data:
retrieving control parameters of the first imaging modality from the three-dimensional image;
selecting a planar transformation based on the control parameters;
projecting the reference surface image data onto a plane corresponding to the slice; and
optimizing the planar transformation to minimize an error level between the slice and the projected reference surface image data;
generate an adjusted three-dimensional image by applying the volume transformation to the three-dimensional image; and
store the adjusted three-dimensional image in the memory.

11. The computing device of claim 10, wherein the first imaging modality is magnetic resonance imaging (MRI).

12. The computing device of claim 10, wherein the second imaging modality is three-dimensional surface scanning.

13. The computing device of claim 10, the processor further configured to determine the surface transformation by:
identifying a plurality of point pairs, each pair including a point in the distorted surface image data and a point in the reference surface image data, each point pair depicting the same portion of the surface of the object; and, for each point pair:

determining a distance between the point in the distorted surface image data and the point in the reference surface image data.

14. The computing device of claim 13, the processor further configured to determine the surface transformation by:

selecting a transformation function; and optimizing the transformation function to minimize the distance.

15. The computing device of claim 10, the processor further configured to:

store, in the memory, a plurality of volume transformations corresponding to different ones of a plurality of surface transformations;

determine the volume transformation by retrieving, from the memory, the volume transformation corresponding to the determined surface transformation.

16. The computing device of claim 10, wherein the volume transformation applies the same transformation function as applied by the surface transformation.

17. The computing device of claim 10, wherein the volume transformation is a localized version of the surface transformation, and wherein applying the volume transformation comprises applying the volume transformation to only a subset of the distorted volume image data.

18. The computing device of claim 10, the processor further configured to:

control the display to present the adjusted three-dimensional image.

* * * * *